United States Patent
Devin-Baudoin

US007824664B2

(10) Patent No.: US 7,824,664 B2
(45) Date of Patent: Nov. 2, 2010

(54) SEMIPERMANENT HAIR SHAPING METHOD

(75) Inventor: Priscille Devin-Baudoin, Vanves (FR)

(73) Assignee: L'Oreal S.A., Paris (FR)

( * ) Notice: Subject to any disclaimer, the term of this patent is extended or adjusted under 35 U.S.C. 154(b) by 660 days.

(21) Appl. No.: 11/414,181

(22) Filed: May 1, 2006

(65) Prior Publication Data

US 2006/0263316 A1 Nov. 23, 2006

Related U.S. Application Data

(60) Provisional application No. 60/726,211, filed on Oct. 14, 2005.

(30) Foreign Application Priority Data

Apr. 29, 2005 (FR) ................................. 05 51134

(51) Int. Cl.
*A61Q 5/06* (2006.01)
(52) U.S. Cl. ............... 424/70.12; 424/70.11; 424/70.16
(58) Field of Classification Search ........................ None
See application file for complete search history.

(56) References Cited

U.S. PATENT DOCUMENTS

| | | | |
|---|---|---|---|
| 2,047,398 A | 7/1936 | Voss et al. | |
| 2,723,248 A | 11/1955 | Wright | |
| 3,836,537 A | 9/1974 | Boerwinkle | |
| 3,925,542 A | 12/1975 | Viout et al. | |
| 3,946,749 A | 3/1976 | Papantoniou | |
| 3,966,403 A | 6/1976 | Papantoniou et al. | |
| 3,966,404 A | 6/1976 | Papantoniou et al. | |
| 3,990,459 A | 11/1976 | Papantoniou | |
| 4,049,007 A * | 9/1977 | Russell et al. ............... | 132/203 |
| 4,070,533 A | 1/1978 | Papantoniou et al. | |
| 4,076,912 A | 2/1978 | Papantoniou et al. | |
| 4,128,631 A | 12/1978 | Lundmark et al. | |
| 4,129,711 A | 12/1978 | Viout et al. | |
| 4,137,208 A | 1/1979 | Elliott | |
| 4,240,450 A * | 12/1980 | Grollier et al. ............... | 132/209 |
| 4,282,203 A | 8/1981 | Jacquet et al. | |
| 4,289,752 A | 9/1981 | Mahieu et al. | |
| 4,348,202 A | 9/1982 | Grollier et al. | |
| 4,366,827 A | 1/1983 | Madrange et al. | |
| 4,579,732 A | 4/1986 | Grollier et al. | |
| 4,660,580 A | 4/1987 | Hoch et al. | |
| 4,693,935 A | 9/1987 | Mazurek | |
| 4,728,571 A | 3/1988 | Clemens et al. | |
| 4,777,040 A | 10/1988 | Grollier et al. | |
| 4,972,037 A | 11/1990 | Garbe et al. | |
| 5,225,191 A | 7/1993 | de Labbey | |
| 6,228,352 B1 * | 5/2001 | Leet ......................... | 424/70.16 |
| 6,372,876 B1 * | 4/2002 | Kim et al. ...................... | 528/71 |
| 6,471,953 B1 | 10/2002 | N'Guyen et al. | |
| 2004/0028632 A1 * | 2/2004 | Maillefer et al. ............ | 424/70.2 |
| 2005/0074418 A1 | 4/2005 | Campain et al. | |

FOREIGN PATENT DOCUMENTS

| | | |
|---|---|---|
| DE | 2 330 956 | 1/1974 |
| EP | 0 412 704 A2 | 2/1991 |
| EP | 0 412 707 A2 | 2/1991 |
| EP | 0 582 152 A2 | 2/1994 |
| EP | 1 064 921 A1 | 1/2001 |
| EP | 1 506 768 A1 | 2/2005 |
| FR | 1 222 944 | 6/1960 |
| FR | 1 400 366 | 4/1965 |
| FR | 1 564 110 | 3/1969 |
| FR | 1 580 545 | 9/1969 |
| FR | 2 102 113 | 4/1972 |
| FR | 2245339 * | 4/1975 |
| FR | 2 265 781 | 10/1975 |
| FR | 2 265 782 | 10/1975 |
| FR | 2 350 384 | 12/1977 |
| FR | 2 439 798 | 5/1980 |
| FR | 2 465 478 | 3/1981 |
| FR | 2 495 931 | 6/1982 |
| GB | 839 805 | 6/1960 |
| GB | 922 457 | 4/1963 |

(Continued)

OTHER PUBLICATIONS

French Search Report for FR 051134, dated Dec. 9, 2005.

(Continued)

*Primary Examiner*—Jyothsna A Venkat
(74) *Attorney, Agent, or Firm*—Finnegan, Henderson, Farabow, Garrett & Dunner, LLP

(57) ABSTRACT

Disclosed herein is a semi-permanent hair shaping method comprising
  (c) applying onto the hair a first composition comprising, in a cosmetically acceptable medium, at least one solubilized fixing polymer chosen from anionic and amphoteric polymers, said application being optionally followed by a resting time for said first composition,
  (d) applying onto the hair a second composition comprising, in a cosmetically acceptable medium, at least 0.15% by weight, relative to the total weight of said second composition, of at least one salt chosen from mineral and organic salts, said application being optionally followed by a resting time for said second composition,
  where step b) is conducted prior to or after step a), then
  (c) rinsing the hair,
  (d) shaping the hair either after applying the first composition of step a), or after applying the second composition of step b) and prior to the rinsing step c).

14 Claims, No Drawings

FOREIGN PATENT DOCUMENTS

| | | |
|---|---|---|
| GB | 1 021 400 | 3/1966 |
| GB | 1 169 862 | 11/1969 |
| GB | 1 334 416 | 10/1973 |
| GB | 2 025 228 A | 1/1980 |
| GB | 1 572 626 | 7/1980 |
| LU | 75370 | 7/1976 |
| LU | 75371 | 7/1976 |
| WO | WO 93/23009 | 11/1993 |
| WO | WO 93/23446 | 11/1993 |
| WO | WO 95/00578 | 1/1995 |
| WO | WO 95/03776 | 2/1995 |

OTHER PUBLICATIONS

English language abstract of FR 2 245 339, Apr. 25, 1975.
English language abstract of FR 2 357 241, Feb. 3, 1978.
English language abstract of FR 2 514 640, Apr. 22, 1983.

* cited by examiner

SEMIPERMANENT HAIR SHAPING METHOD

This application claims benefit of U.S. Provisional Application No. 60/726,211, filed Oct. 14, 2005, the contents of which are incorporated herein by reference. This application also claims benefit of priority under 35 U.S.C. §119 to French Patent Application No. 05 51134, filed Apr. 29, 2005, the contents of which are also incorporated herein by reference.

The present invention relates to a method for shaping the hair.

There are two main classes of products that are typically used for shaping the hair: hair styling products and permanenting products.

The styling products typically make it possible to reshape the hair non-permanently. They may be used on wet or dry hair prior to being shaped with, for example, the hand, a brush or a comb. After their application onto the hair, and once they have been dried, these products may substantially harden. This hardening may express as a texturized and dry feel that is necessary for retaining and volumizing the hair style. Such styling products, however, are usually washed out after even one shampoo and hence have to be applied every day.

Permanenting products may enable a longer lasting hair shaping. Traditionally, the practice used to obtain a permanent reshaping of the hair comprises, in a first step, opening the keratin —S—S— disulfide bonds (cystine) by applying onto hair which has been placed beforehand under tension (with rollers or equivalent suitable means) a reducing composition (reducing step), then optionally after having rinsed the so treated hair, re-forming in a second step said disulfide bonds by applying onto the hair still remaining under tension an oxidizing composition (oxidizing step, also called fixing step) so as to finally give to the hair the desired form.

The new shape that has been imposed to the hair by means of a chemical treatment as described above is long lasting and does resist the effect of washing with water or shampoos. However, such a method is not always fully satisfactory. While it is indeed very efficient to reshape the hair, it may cause great damage to the hair fibers.

There is therefore a need to have a method that is fast and easy to use, that is not aggressive to the hair and/or that provides the hair with good hold while being remanent with respect to shampoo, and wherein the hair has a good cosmetic quality, for example, as regards softness, shine and/or non-sticky feel. Shine and feel properties may be improved as compared to a styling product, and fiber integrity and color may be improved as compared to a permanenting product.

A two-part fixing product is known from French Patent No. FR 2 245 339, to be applied simultaneously or consecutively, the first part being an alkaline silicate or an aluminium salt-comprising solution, and the second part being a solution comprising a polymer used at an acidic or alkaline pH value. These two solutions, by interacting with each other, result in a silicic acid or aluminium hydrate-based precipitate, laid down onto the hair.

A hair treating composition is also known from British Patent No. GB 2 025 228 that comprises a mixture of a cationic polymer and an anionic polymer, said cationic and anionic polymers being suitable for producing a complex that will precipitate on the hair in the presence of a calcium salt.

However, neither system provides for sufficient cosmeticity and/or durability of the resulting effect.

Disclosed herein, therefore, is a new hair-shaping method comprising
(a) applying onto the hair a first composition comprising, in a cosmetically acceptable medium, at least one solubilized fixing polymer chosen from anionic and amphoteric polymers, said application optionally being followed by a resting time for said first composition,
(b) applying onto the hair a second composition comprising, in a cosmetically acceptable medium, at least 0.15% by weight, relative to the total weight of said second composition, of at least one mineral or organic salt, said application optionally being followed by a resting time for said second composition,
where step b) is conducted prior to or after step a), then
(c) rinsing the hair, and
(d) shaping the hair either after applying the first composition of step a), or after applying the second composition of step b) and prior to the rinsing step c).

This resting time for the first or the second composition may occur at room temperature or by heating at a temperature ranging from 30 to 250 C, such heating being provided by, for example, a hair drier, a hood, a straightening iron or a curling iron or by means of a steam generating or an IR generating device.

The thus obtained hair shape is remanent with respect to at least one shampoo, for example, with respect to at least two shampoos.

According to one embodiment, the method of the present disclosure neither comprises any step of opening the hair keratin disulfide bonds by means of a reducing composition, nor any step of re-forming said disulfide bonds by means of an oxidizing composition.

Fixing Polymers

As used herein, a "fixing polymer" means any polymer that can give the hair a shape or that can modify the shape of said hair.

As mentioned above, the at least one fixing polymer is chosen from anionic and amphoteric polymers.

In at least one embodiment, the composition of step (a), for example, may not comprise any cationic polymer.

Anionic Fixing Polymers

Anionic polymer useful herein include, but are not limited to, polymers comprising groups chosen from carboxylic, sulfonic and phosphoric acid derived groups and having a weight average molecular weight ranging from 500 to 5 000 000.

Carboxylic groups may be chosen, for example, from those provided by unsaturated, carboxylic, monoacidic or diacidic monomers, such as, for example, those having following formula:

$$\begin{array}{c} R_1 \\ \diagdown \\ R_2 \end{array} C = C \begin{array}{c} (A)_n - COOH \\ \diagup \\ R_3 \end{array} \quad (I)$$

wherein
n is an integer ranging from 0 to 10,
A is a methylene group, optionally bound to the carbon atom of the unsaturated group or to the adjacent methylene group when n is more than 1, through a heteroatom such as oxygen or sulfur,
$R'_1$ is chosen from hydrogen atoms, phenyl groups and benzyl groups,
$R'_2$ is chosen from hydrogen atoms, lower alkyl groups and carboxyl groups,
$R'_3$ is chosen from hydrogen atoms, lower alkyl groups, —$CH_2$—COOH, phenyl groups and benzyl groups.

In the above formula (I), a lower alkyl group may, for example, comprise from 1 to 4 carbon atoms, for example, methyl and ethyl groups.

Non-limiting examples of carboxylic or sulfonic group-containing anionic polymers according to the present disclosure include:

A) homo- or copolymers of acrylic or methacrylic acid or salts thereof, including copolymers of acrylic acid and acrylamide and copolymers of methacrylic acid and acrylic acid/ethyl acrylate/methyl methacrylate, for example, AMERHOLD DR25 marketed by AMERCHOL and sodium salts of polyhydroxycarboxylic acids. Suitable are also copolymers of methacrylic acid/ethyl acrylate, for example, in aqueous dispersion, such as LUVIFLEX SOFT and LUVIMER MAE marketed by BASF.

B) Acrylic or methacrylic acid copolymers with a monoethylene monomer such as, for example, ethylene, styrene, vinyl esters, acrylic or methacrylic acid esters, optionally grafted to a polyalkylene glycol such as polyethylene glycol, and optionally crosslinked. Such polymers are described, for example, in French Patent No. 1,222,944 and in German Patent Application No. 2,330,956, copolymers of this type comprising in their chain an optionally N-alkylated and/or hydroxyalkylated acrylamide unit, such as described in Luxembourg Patent Application Nos. 75370 and 75371. Copolymers of acrylic acid and $C_1$-$C_4$ alkyl methacrylate may, for example, also be mentioned.

C) Copolymers derived from crotonic acid such as those comprising in their chain vinyl acetate or vinyl propionate units and optionally other monomers such as allyl or methallyl esters, vinyl ethers or vinyl esters of a saturated, linear or branched carboxylic acid with a long hydrocarbon chain, such as those having at least 5 carbon atoms, where such polymers may be optionally grafted and crosslinked, or a vinyl, allyl or methallyl ester of a α or β-cyclic carboxylic acid. Such polymers are described, for example, in French Patent Nos. 1,222,944, 1,580,545, 2,265,782, 2,265,781, 1,564,110 and 2,439,798. Commercial products belonging to this class are 28-29-30 resins, 26-13-14 resins and 28-13-10 resins marketed by NATIONAL STARCH. Additional crotonic acid derived copolymers may include terpolymers of crotonic acid, vinyl acetate and vinyl tert.-butylbenzoate, for example, MEXOMERE PW marketed by CHIMEX.

D) Polymers derived from maleic, fumaric, itaconic acids or anhydrides with vinyl esters, vinyl ethers, vinyl halides, phenyl vinyl derivatives, acrylic acid and esters thereof; these polymers may be esterified. Such polymers are, for example, described in U.S. Pat. Nos. 2,047,398, 2,723,248, and 2,102,113 and in British Patent Nos. GB 839,805, and, for example, those marketed under the trade names GANTREZ® AN or ES by ISP. Polymers also belonging to this class include copolymers of maleic, citraconic, itaconic anhydride and an allyl or methallyl ester, optionally comprising in their chain an acrylamide, methacrylamide group, an α-olefin, acrylic or methacrylic esters, acrylic or methacrylic acids or vinyl pyrrolidone, the anhydride functionalities being monoesterified or monoamidified. These polymers are described, for example, in French Patent Nos. 2,350,384 and 2,357,241.

E) Polyacrylamides comprising carboxylate groups.

F) Polymers comprising sulfonic groups. These polymers may be polymers comprising vinyl sulfonic, styrene-sulfonic, naphthalene-sulfonic, acrylamido-alkyl sulfonic, sulfoisophthalate units.

These polymers may be, for example, chosen from:

polyvinylsulfonic acid salts having a molecular weight ranging from 1 000 to 100 000, as well as copolymers with an unsaturated comonomer such as acrylic or methacrylic acids, and esters thereof, as well as acrylamide or derivatives thereof, vinyl ethers and vinyl pyrrolidone;

polystyrene-sulfonic acid salts, sodium salts, having a molecular weight ranging from 500 000 to 100 000. These compounds are described in the French Patent No. FR 2,198,719.

polyacrylamide-sulfonic acid salts such as those mentioned in U.S. Pat. No. 4,128,631;

G) anionic silicone graft polymers;

The silicone graft polymers used herein may be, for example, chosen from polymers having an organic non-silicone backbone grafted with monomers comprising a polysiloxane, polymers having a polysiloxane backbone grafted with non-silicone organic monomers, and mixtures thereof.

"Silicone" or "polysiloxane" as used herein, means any oligomeric organosilicone polymer of variable molecular weight having a linear or cyclic, branched or crosslinked structure, that are obtained by polymerization and/or polycondensation of silanes suitably functionalized and substantially made of repeating main units wherein silicon atoms are bound with each other through oxygen atoms (siloxane bond ≡Si—O—Si≡), optionally substituted hydrocarbon radicals being directly bound through a carbon atom on said silicon atoms. Examples of common hydrocarbon radicals include alkyl radicals, for instance, $C_1$-$C_{10}$ alkyl radicals, such as methyl; fluoralkyl; aryl radicals such as phenyl radicals; and alkenyl radicals such as vinyl radicals. Other types of radicals that may be bound to the siloxane chain either directly or through a hydrocarbon radical may be, for example, chosen from hydrogen, halogen, for example, chlorine, bromine or fluorine, thiols, alkoxy radicals, polyoxyalkylene radicals (or polyethers), for example, polyoxyethylene and/or polyoxypropylene radicals, hydroxyl or hydroxyalkyl radicals, substituted or not substituted amine groups, amide groups, acyloxy or acyloxyalkyl radicals, hydroxyalkylamino or aminoalkyl radicals, quaternary ammonium groups, amphoteric or betaine groups, anionic groups such as carboxylates, thioglycolates, sulfosuccinates, thiosulfates, phosphates and sulfates, this list of course not being limitative in any way (silicones that are said to be "organomodified").

As used herein, "polysiloxane macromer" means, any monomer having in its structure a polysiloxane type polymer chain.

Polymers with an organic non-silicone backbone, grafted with monomers comprising a polysiloxane used according to the present disclosure comprise an organic main chain formed from organic monomers with no silicone, on which at least one polysiloxane macromer is grafted, within said chain as well as optionally on at least one end thereof.

Non-silicone organic monomers comprising the main chain of the graft silicone polymer may be, for example, chosen from ethylenically unsaturated monomers that may be free-radical polymerized, polycondensation polymerizable monomers such as those forming polyamides, polyesters, polyurethanes, ring opening monomers such as those of the oxazoline or caprolactone type.

Polymers with a non-silicone organic backbone grafted with monomers comprising a polysiloxane in accordance with the present disclosure may be obtained by any method known from the one skilled in the art, for example, by producing a reaction between (i) a starting polysiloxane macromer suitably functionalized on the polysiloxane chain, and (ii) at least one organic, non-silicone compound, that are themselves suitably functionalized with a functionality which can react with the at least one functional group carried by said silicone by forming a covalent bond; a non-limiting example of such a reaction is the free-radical reaction of a vinyl group carried on one end of the silicone with a double bond of a main chain ethylenically unsaturated monomer.

In at least one embodiment, polymers with a non-silicone organic backbone grafted with monomers comprising a polysiloxane may be, for example, chosen from those described in U.S. Pat. Nos. 4,693,935, 4,728,571 and 4,972,037 and in European Patent Application Nos. EP-A-0 412 704, EP-A-0 412 707, and EP-A-0 640 105 and International Published Application No. WO 95/00578. There are copolymers obtained by free-radical polymerization from ethylenically unsaturated monomers and from silicone macromers having a vinyl terminal group, or copolymers obtained by reacting a polyolefin comprising functionalized groups with a polysiloxane macromer having a terminal functionality reactive towards said functionalized groups.

In at least one embodiment, the graft silicone polymer family may be chosen from silicone graft copolymers comprising:
a) from 0 to 98% by weight of at least one lipophilic, weakly polar, ethylenically unsaturated, free-radical polymerizable monomer (A);
b) from 1 to 98% by weight of at least one hydrophilic, polar, ethylenically unsaturated monomer (B), copolymerizable with the at least one monomer of type (A);
c) from 0.01 to 50% by weight of at least one polysiloxane macromer (C) having following formula:

$$X(Y)_n Si(R)_{3-m} Z_m \qquad (II)$$

wherein:
X is chosen from vinyl groups that are copolymerizable with monomers (A) and (B);
Y is chosen from divalent binding groups;
R is chosen from hydrogen, $C_1$-$C_6$ alkyl or alkoxy groups, and $C_6$-$C_{12}$ aryl groups;
Z is chosen from monovalent polysiloxane units having a number average molecular weight of at least 500;
n is 0 or 1, and
m is an integer ranging from 1 to 3;
percentages being expressed as compared to the total weight of monomers (A), (B) and (C).

For example, these polymers are described together with their preparation methods in the U.S. Pat. Nos. 4,963,935, 4,728,571 and 4,972,037 and the European Patent Application Nos. EP-A-0 412 704, EP-A-0 412 707, and EP-A-0 640 105. They may, for example, have a number average molecular weight ranging from 10 000 to 2 000 000, and may, for example, have a glass transition temperature or a crystal fusion temperature Tm of at least −20° C.

In at least one embodiment, lipophilic monomers (A) may be chosen from acrylic or methacrylic acid esters of $C_1$-$C_{18}$ alcohols; styrene; polystyrene macromers; vinyl acetate; vinyl propionate; α-methyl styrene; tert.-butyl styrene; butadiene; cyclohexadiene; ethylene; propylene; vinyl toluene; esters of acrylic or methacrylic acid and 1,1-dihydroperfluoroalkanol or homologs thereof; esters of acrylic or methacrylic acid and omega-hydridofluoroalkanol; esters of acrylic or methacrylic acid and fluoroalkyl sulfoamido-alcohol; esters of acrylic or methacrylic acid and fluoroalkyl alcohol; esters of acrylic or methacrylic acid and fluorether alcohol; and mixtures thereof.

Monomers (A) may, for example, be chosen from n-butyl methacrylate, isobutyl methacrylate, tert.-butyl acrylate and methacrylate, 2-ethyl hexyl methacrylate, methyl methacrylate, 2-(N-methyl perfluoroctane sulfoamido)ethyl acrylate; 2-(N-butyl perfluoroctane sulfoamido)ethylacrylate; and mixtures thereof.

In at least one embodiment, polar monomers (B) may, for example, be chosen from acrylic acid, methacrylic acid, NN-dimethyl acrylamide, dimethylaminoethyl methacrylate, quaternized dimethylaminoethyl methacrylate, (meth)acrylamide, N-t-butyl acrylamide, maleic acid, maleic anhydride and half-esters thereof, hydroxyalkylated (meth)acrylates, diallyl dimethyl ammonium chloride, vinyl pyrrolidone, vinyl ethers, maleimides, vinyl pyridine, vinylimidazole, heterocyclic vinyl polar compounds, styrene sulfonate, allyl alcohol, vinyl alcohol, vinyl caprolactame, or mixtures thereof. Monomers (B) may be chosen from, for example acrylic acid, N,N-dimethyl acrylamide, dimethyl aminoethyl methacrylate, quaternized dimethyl aminoethyl methacrylate, vinyl pyrrolidone, and mixtures thereof.

Polar monomers (B) may also, for example, be chosen from anionic silicone graft polymers comprising at least one anionic monomer.

In at least one embodiment, polysiloxane macromers (C) of formula (II) may be chosen from macromers of formula (III):

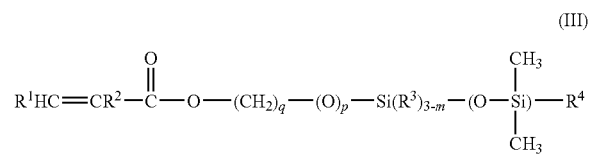

wherein:
$R_1$ is chosen from hydrogen and —COOH and in at least one embodiment is hydrogen;
$R_2$ is chosen from hydrogen, methyl groups and —$CH_2$COOH and in at least one embodiment is methyl;
$R_3$ is chosen from $C_1$-$C_6$ alkyl, $C_1$-$C_6$ alkoxy, $C_1$-$C_6$ alkylamino, $C_1$-$C_{12}$ aryl and hydroxyl groups, and in at least one embodiment is a methyl group;
$R_4$ is chosen from $C_1$-$C_6$ alkyl, $C_1$-$C_6$ alkoxy, $C_1$-$C_6$ alkylamino, $C_1$-$C_{12}$ aryl and hydroxyl groups, and in at least one embodiment is a methyl group;
q is an integer ranging from 2 to 6, for example, 3;
p is 0 or 1;
r is an integer ranging from 5 to 700;
m is an integer ranging from 1 to 3 and in at least one embodiment m is 1;
In at least one embodiment, polysiloxane macromers are used that have the following formula:

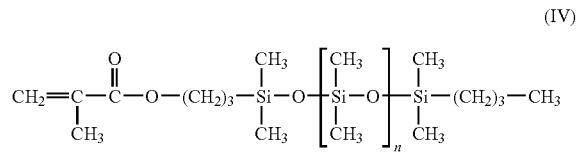

wherein n is an integer ranging from 5 to 700.

In at least one embodiment, a copolymer may be used that may be obtained by free-radical polymerization from a mixture of monomers made of:

a) 60% by weight of tert.-butyl acrylate;
b) 20% by weight of acrylic acid;
c) 20% by weight of silicone macromer having the following formula:

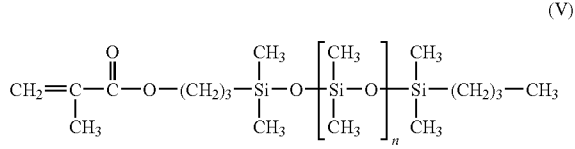

(V)

wherein n is an integer ranging from 5 to 700 and
weight percentages being expressed as compared to the total weight of the monomers.

In at least one embodiment, suitable silicone polymers may be chosen from silicone graft copolymers that may be obtained by a reactive extrusion of a polysiloxane macromer having a reactive end functionality on an olefin type-polymer comprising reactive groups that may react with the polysiloxane macromer end functionality to form a covalent bond, making it possible to graft the silicone on the polyolefin main chain.

These polymers together with their production methods are described, for example, in International Published Patent Application No. WO 95/00578.

In at least one embodiment, reactive polyolefins may be chosen from polyethylenes or polymers of ethylene-derived monomers such as propylene, styrene, alkyl styrenes, butylene, butadiene, (meth)acrylates, vinyl esters or equivalents, comprising reactive functionalities that may react with the polysiloxane macromer end functionality. The reactive polyolefins may, for example, be chosen from copolymers of ethylene or ethylene derivatives and of monomers chosen from those comprising a carboxyle functionality, such as (meth)acrylic acid; those comprising an acid anhydride functionality such as maleic acid anhydride; those comprising an acid chloride functionality, such as (meth)acrylic acid chloride; those comprising an ester functionality, such as (meth)acrylic acid esters; those comprising an isocyanate functionality.

In at least one embodiment, silicone macromers may be chosen from polysiloxanes comprising a functionalized group at the end of the polysiloxane chain or close to said chain end, chosen from alcohols, thiols, epoxies, primary and secondary amines, and, for example, those the having following formula (VI):

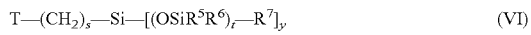

(VI)

wherein
T is chosen from $NH_2$, NHR', an epoxy functionality, OH, and SH;
$R^5$, $R^6$, $R^7$ and R', which may be the same or different, are each chosen from $C_1$-$C_6$ alkyl, phenyl, benzyl, $C_6$-$C_{12}$ alkyl phenyl groups and from hydrogen;
s is a number ranging from 2 to 100;
t is a number ranging from 0 to 1000; and
y is a number ranging from 1 to 3.

In at least one embodiment, the silicone macromers may, for example, be chosen from macromers having a number average molecular weight ranging from 5 000 to 300 000, for example, from 8 000 to 200 000 and further, for example, from 9 000 to 40 000.

In at least one embodiment, the at least one silicone graft polymer having a polysiloxane backbone grafted with at least one non-silicone organic monomer comprises a silicone main chain (or polysiloxane ($\equiv$Si—O—$)_n$) on which at least one organic group with no silicone is grafted within said chain as well as optionally on at least one end thereof.

In one embodiment, polymers having a polysiloxane backbone grafted with non-silicone organic monomers may be chosen from existing commercial products or may also be obtained by any method to one skilled in the art, for example, by conducting a reaction between (i) a starting silicone that is suitably functionalized on at least one silicon atoms and (ii) a non-silicone organic compound that itself is suitably functionalized by a functionality which can react with the at least one functional moiety that is carried on said silicone by forming a covalent bond; such usual reaction may be exemplified by a hydrosylilation reaction between $\equiv$Si—H groups and $CH_2$=CH— vinyl groups, or by the reaction occurring between thio-functional SH groups with such vinyl groups.

Non-limiting examples of polymers having a polysiloxane backbone grafted with non-silicone organic monomers useful herein, as well as their particular preparation mode, are described, for example, in European Patent Application No. EP-A-0 582 152, and International Published Application Nos. WO 93/23009 and WO 95/03776, the teachings of which are incorporated by reference herein.

According to at least one embodiment, the silicone polymer having a polysiloxane backbone grafted with non-silicone organic monomers as implemented may comprise the free-radical copolymerization result between, on the one hand, at least one ethylenically unsaturated non-silicone, anionic, organic monomer and/or an ethylenically unsaturated non-silicone hydrophobic, organic monomer, and on the other hand, a silicone comprising in its chain at least one functional group that can react on said ethylene unsaturations of said non-silicone monomers by forming a covalent bond, for example, thio-functional groups.

According to at least one embodiment, said ethylenically unsaturated anionic monomers may be chosen from unsaturated, linear or branched carboxylic acids that are optionally partly or fully neutralized as a salt, for example, acrylic acid, methacrylic acid, maleic acid, maleic anhydride, itaconic acid, fumaric acid and crotonic acid. Suitable salts may be, for example, chosen from alkaline metal salts, earth-metal salts and ammonium salts. In at least one embodiment, in the final silicone graft polymer, the anionic in nature organic group comprising the result from the free-radical (homo)polymerization of at least one anionic monomer of the unsaturated carboxylic acid type may be post neutralized after the reaction with a base (for example, soda or ammonia) to be converted as a salt.

According to the present disclosure, ethylenically unsaturated hydrophobic monomers may, in one embodiment, be chosen from, alone or as a mixture, acrylic acid esters of alkanols and/or methacrylic acid esters of alkanols. The alkanols may be chosen from those comprising from 1 to 18, for example, from 1 to 12 carbon atoms. In at least one embodiment, monomers may be chosen from isooctyl(meth) acrylate, isononyl (meth)acrylate, 2-ethylhexyl(meth)acrylate, lauryl(meth)acrylate, isopentyl(meth)acrylate, n-butyl (meth)acrylate, isobutyl(meth)acrylate, methyl(meth) acrylate, tert.-butyl (meth)acrylate, tridecyl(meth)acrylate, stearyl(meth)acrylate and mixtures thereof.

In at least one embodiment, a silicone polymer family with a polysiloxane backbone grafted with non-silicone organic monomers may be chosen from silicone polymers comprising within their structure the unit of following formula (VII):

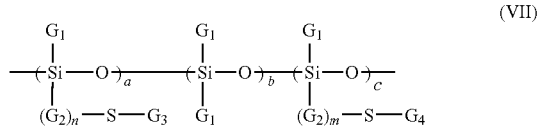 (VII)

wherein
$G_1$ radicals, which may be the same or different, are each chosen from hydrogen, $C_1$-$C_{10}$ alkyl groups and phenyl groups;
$G_2$ radicals, which may be the same or different, are each chosen from $C_1$-$C_{10}$ alkyl groups;
$G_3$ is chosen from polymer radicals resulting from the (homo)polymerization of at least one ethylenically unsaturated anionic monomer;
$G_4$ is chosen from polymer radicals resulting from the (homo) polymerization of at least one ethylenically unsaturated hydrophobic monomer;
m and n are 0 or 1;
a is an integer ranging from 0 to 50;
b is an integer ranging from 10 to 350; and
c is an integer ranging from 0 to 50;
provided one of a and c is different from 0.

In at least one embodiment, the unit of the above formula (IV) presents at least one of, and for example all of, the following characteristic feature(s):
$G_1$ radicals are chosen from alkyl radicals, for example, methyl radicals;
n is different from 0 and
$G_2$ radicals are chosen from $C_1$-$C_3$ divalent radicals, for example, propylene radicals;
$G_3$ is chosen from polymer radicals resulting from the (homo)polymerization of at least one monomer of the ethylenically unsaturated carboxylic acid type, for example, acrylic acid and/or methacrylic acid;
$G_4$ is chosen from polymer radicals resulting from the (homo)polymerization of at least one monomer of the $C_1$-$C_{10}$ alkyl methacrylate type, for example, isobutyl or methyl(meth)acrylate.

Examples of silicone graft polymers of formula (IV) include, for example, polydimethyl siloxanes (PDMS) on which mixed polymer units of the poly(meth)acrylic acid type and of the methyl poly(meth)acrylate type are grafted through a binding chain member of the thiopropylene type.

In at least one embodiment, the number average molecular weight of silicone polymers having a polysiloxane backbone grafted with non-silicone organic monomers ranges from 10 000 to 1 000 000, for example, from 10 000 to 100 000.

Graft silicone polymers that can be used herein may be, for example, chosen from the product marketed by 3M under the trade name VS80.

H) Anionic Polyurethanes.

In at least one embodiment, polyurethanes useful herein may be chosen from those having a basic repeating unit of formula (VII):

—X'—B—X'—CO—NH—R—NH—CO— (VII)

wherein
X' is chosen from O and NH,
B is chosen from substituted or unsubstituted, divalent hydrocarbon radicals and
R is chosen from divalent radicals chosen from branched and unbranched, alkylene radicals, of $C_6$-$C_{20}$ aromatic type, $C_1$-$C_{20}$ aliphatic type, for example, $C_1$-$C_6$, $C_1$-$C_{20}$ cycloaliphatic type, further, for example, $C_1$-$C_6$, optionally substituted by at least one group chosen from halogen, $C_1$-$C_4$ alkoxy, $C_6$-$C_{30}$ aryl, for example, phenyl groups.

In at least one embodiment, radical B may be chosen from $C_1$-$C_{30}$ divalent radicals, for example, $C_2$-$C_{10}$, and carries a group comprising at least one carboxylic functionality and/or at least one sulfonic functionality, said carboxylic and/or sulfonic functionalities being in the free form or being partly or fully neutralized by means of a mineral or organic base such as alkaline metal or alkaline earth metal hydroxides, ammonia and alkyl amines or alkanol amines, as well as organic aminoacids. For example, B may be chosen from the divalent radical derived from dimethylol propionic acid.

In at least one embodiment, the radical R may be chosen from radicals having following formulas:

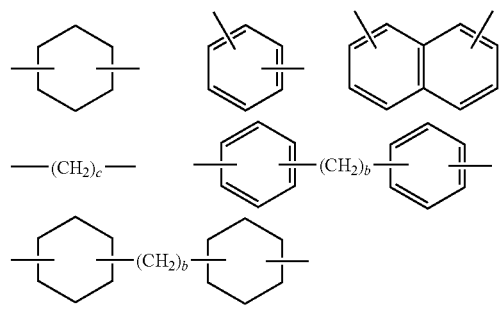

wherein
b is chosen from an integer ranging from 0 to 3 and
c is chosen from an integer ranging from 1 to 20, for example, from 2 to 12.

In at least one embodiment, the radical R may be chosen from hexamethylene, 4,4'-biphenylene methane, 2,4 and/or 2,6-tolylene, 1,5-naphthylene, p-phenylene, methylene-4, 4bis-cyclohexyl radicals, and the divalent radical derived from isophorone.

In at least one embodiment, fixing polyurethanes may comprise silicone grafts and hydrocarbon graft silicones.

In at least one embodiment, a polyurethane used herein may comprise at least one polysiloxane sequence, which basic repeating unit has, for example, the following formula (IX):

—X'—P—X'—CO—NH—R—NH—CO— (IX)

wherein:
P is a polysiloxane segment,
X' is chosen from O and NH, and
R is a divalent radical chosen from branched and unbranched, alkylene radicals; $C_6$-$C_{20}$ aromatic types; $C_1$-$C_{20}$ aliphatic types, for example $C_1$-$C_6$; $C_1$-$C_{20}$ cycloaliphatic types, for example, $C_1$-$C_6$; optionally substituted with at least one halogen, $C_1$-$C_4$ alkoxy, and $C_1$-$C_{30}$ aryl, for example, phenyl groups.

In at least one embodiment, the radical R may be chosen from radicals having the following formulas:

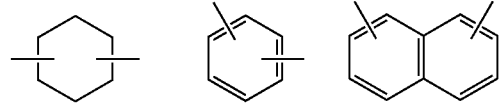

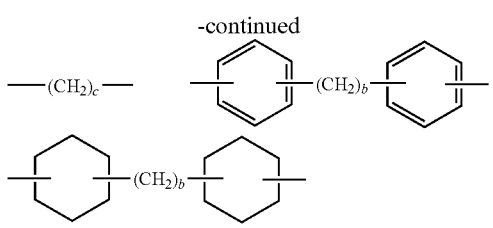

wherein
b is an integer ranging from 0 to 3, and
c is an integer ranging from 1 to 20, for example, from 2 to 12.

In at least one embodiment, the radical R may be chosen from hexamethylene, 4,4'-biphenylene methane, 2,4 and/or 2,6-tolylene, 1,5-naphthylene, p-phenylene, methylene-4, 4bis-cyclohexyl radicals, and the divalent radical derived from isophorone.

In at least one embodiment, the polysiloxane segment P may be chosen from a segment of formula (X):

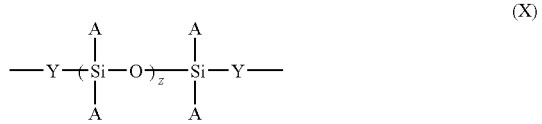

wherein:
A, which may be identical or different, is chosen from $C_1$-$C_{20}$ monovalent hydrocarbon groups, substantially free from any ethylenic unsaturation, and from aromatic groups,
Y is a divalent hydrocarbon group, and
Z is an integer chosen so as the polysiloxane segment mean molecular weight ranges from 300 to 10 000.

In at least one embodiment, divalent group Y may be chosen from alkylene groups of formula —$(CH_2)_a$—, wherein a is chosen from an integer ranging from 1 to 10.

In at least one embodiment, A may be chosen from $C_1$-$C_{18}$ alkyl groups, for example, methyl, ethyl, propyl, isopropyl, butyl, pentyl, hexyl, octyl, decyl, dodecyl and octadecyl groups; cycloalkyl groups, for example, cyclohexyl; aryl groups; for example, phenyl and naphthyl groups; arylalkyl groups, further, for example, benzyl and phenyl ethyl, as well as tolyl and xylyl groups.

Examples of suitable fixing polyurethanes include, for example, the copolymer of dimethylol propionic acid/diisocyanate isophorone/neopentyl glycol/polyester diols (also known under the INCI name polyurethane-1) sold under the trade name Luviset® PUR by BASF, the copolymer of dimethylol propionic acid/diisocyanate isophorone/neopentyl glycol/polyester diols/silicone diamine (also known under the INCI name polyurethane-6) sold under the trade name Luviset®Si PUR A by BASF.

Sulfoisophthalate group polymers, for example, may also be used, such as AQ55 and AQ48 polymers, marketed by EASTMAN.

In at least one embodiment, anionic polymers may be chosen from acrylic acid copolymers such as the terpolymer of acrylic acid/ethyl acrylate/N-tert.-butyl acrylamide sold under the trade name ULTRAHOLD STRONG® by BASF, copolymers of methacrylic acid and ethyl acrylate, for example, in aqueous dispersion, such as LUVIFLEX SOFT and LUVIMER MAE marketed by BASF. Copolymers derived from crotonic acid, such as terpolymers of vinyl acetate/vinyl tert.-butyl benzoate/crotonic acid, as well as terpolymers of crotonic acid/vinyl acetate/vinyl neododecanoate sold under the trade name Resin 28-29-30 by NATIONAL STARCH, polymers derived from maleic, fumaric and itaconic acids or anhydrides with vinyl esters, vinyl ethers, vinyl halides, phenyl vinyl derivatives, acrylic acid and esters thereof such as the copolymer of methylvinyl ether and monoesterified maleic anhydride sold under the trade name GANTREZ®ES 425 by ISP, LUVISET SI PUR, MEXOMERE PW, elastomer or non-elastomer, anionic polyurethanes, sulfoisophthalate group polymers, anionic silicone graft polymers, as well as AMERHOLD DR25 and VS 80.

Amphoteric Fixing Polymers

Amphoteric polymers useful herein may be chosen from polymers having units B and C statistically distributed within the polymer chain, where B is chosen from units derived from a monomer comprising at least one basic nitrogen atom and C is chosen from units derived from an acidic monomer comprising at least one carboxylic or sulfonic moiety, or B and C may be chosen from groups derived from zwitterionic monomers of carboxybetaines or sulfobetaines; B and C may also be chosen from cationic polymer chains comprising primary, secondary, tertiary or quaternary amine groups, where at least one of the amine groups carries a carboxylic or a sulfonic group bound through a hydrocarbon group, or B and C form part of a chain of an ethylene-dicarboxylic unit containing polymer, one of the carboxylic groups of which has been caused to react with a polyamine comprising at least one primary or secondary amine moiety.

In at least one embodiment, amphoteric polymers may be chosen from:

1) polymers resulting from the copolymerization of a monomer derived from a vinyl compound carrying a carboxylic group, such as, for example, acrylic acid, methacrylic acid, maleic acid, alpha-chloracrylic acid, and from a basic monomer derived from a substituted vinyl compound comprising at least one basic atom such as, for example, dialkylaminoalkyl methacrylate and -acrylate, dialkylaminoalkyl methacrylamide and -acrylamide. Such compounds are described in U.S. Pat. No. 3,836,537.

Such vinyl compound may also be chosen from dialkyldiallylammonium salts such as diethyldiallyl-ammonium chloride.

(2) polymers comprising units derived from:
a) at least one monomer chosen from acrylamides and methacrylamides, substituted on the nitrogen with an alkyl group,
b) at least one acidic comonomer comprising at least one reactive carboxylic moiety, and
c) at least one basic comonomer, such as primary, secondary, tertiary and quaternary amine substituted esters of acrylic and methacrylic acids, and the quaternization product of dimethyl aminoethyl methacrylate with dimethyl or diethyl sulfate.

In at least one embodiment, N-substituted acrylamides or methacrylamides that may be used according to the present disclosure include alkyl groups which comprise from 2 to 12 carbon atoms, for example, N-ethyl acrylamide, N-tert.-butyl acrylamide, N-tert.-octyl acrylamide, N-octyl acrylamide, N-decyl acrylamide, and N-dodecyl acrylamide, as well as corresponding methacrylamides.

In at least one embodiment, acidic comonomers may be chosen from acrylic, methacrylic, crotonic, itaconic, maleic and fumaric acids, as well as alkyl monoesters comprising from 1 to 4 carbon atom(s) of maleic or fumaric acids or anhydrides. In at least one embodiment, basic comonomers may be chosen from aminoethyl, butylaminoethyl, N,N'-dimethylaminoethyl and N-tert.-butylaminoethyl methacrylates. Copolymers that may be used in at least one embodiment have a CTFA name (4$^{th}$ ed. 1991) of copolymers of octylacryl amide/acrylates/butylaminoethyl methacrylate, such as the products sold under the trade name AMPHOMER® or LOVOCRYL® 47 by NATIONAL STARCH.

(3) crosslinked and partly or fully alkylated polyaminoamides derived from polyaminoamides of the following formula:

$$\text{---}[\text{CO}\text{---}R_4\text{---}\text{CO}\text{---}Z]\text{---} \quad (XI)$$

wherein $R_4$ is chosen from divalent groups derived from a saturated dicarboxylic acid, from an ethylene double bond containing, aliphatic, mono or -dicarboxylic acid, from an ester of a lower alkanol comprising from 1 to 6 carbon atom(s) of these acids or from a group resulting from the addition of any one of said acids with a bis-primary or bis-secondary derived amine, and Z is chosen from a group of a polyalkylene-bis-primary, mono- or bis-secondary polyamine, and is, for example, chosen from:

a) in amounts ranging from 60 to 100 mol. %, the group $$\text{---}\text{NH}\text{---}[(CH_2)_x\text{---}\text{NH}]_p\text{---} \quad (XII)$$

wherein x is 2 and p is 2 or 3, or x is 3 and p is 2, this group being derived from diethylene triamine, triethylene tetraamine or dipropylene triamine;

b) in amounts ranging from 0 to 40 mol. %, the above group (XII), wherein x is 2 and p is 1, being derived from ethylene diamine, or the group derived from piperazine $$\text{---}N\diagup\diagdown N\text{---}$$

c) in amounts ranging from 0 to 20 mol. %, the —NH—(CH$_2$)$_6$—NH group derived from hexamethylene diamine, these polyaminoamines being crosslinked by adding a difunctional crosslinking agent chosen from epihalohydrines, diepoxies, dianhydrides, unsaturated bis-derivatives, by means of 0.025 to 0.35 mole of a crosslinking agent per amine group of the polyaminoamide and alkylated by the action of acrylic acid, chloracetic acid or by means of an alkane-sultone, or their salts.

In at least one embodiment, saturated carboxylic acids may be chosen from acids ranging from 6 to 10 carbon atoms, such as adipic acid, 2,2,4-trimethyl adipic acid, and 2,4,4-trimethyl adipic acid, terephthalic acid, ethylene double-bond acids such as, for example, acrylic, methacrylic and itaconic acids. Alkane sultones used for the alkylation may be chosen from propane or butane sultone, and alkylating agent salts may be chosen from sodium and potassium salts.

(4) Polymers comprising zwitterionic units of formula:

$$R_5\text{---}\left[\begin{array}{c}R_6\\|\\C\\|\\R_7\end{array}\right]_y\text{---}\begin{array}{c}R_8\\|\\N^+\\|\\R_9\end{array}\text{---}(CH_2)_z\text{---}\overset{O}{\overset{\|}{C}}\text{---}O^- \quad (XIII)$$

wherein $R_5$ is a polymerizable unsaturated group such as an acrylate, methacrylate, acrylamide or methacrylamide group, y and z, which may be identical or different, are each an integer ranging from 1 to 3, $R_6$ and $R_7$, which may be identical or different, are each chosen from hydrogen atoms, methyl groups, ethyl groups and propyl groups, $R_8$ and $R_9$, which may be identical or different, are each chosen from hydrogen atoms and alkyl group, so that the sum of the carbon atoms contained in $R_8$ and $R_9$ does not exceed 10.

In at least one embodiment, polymers comprising such units may also comprise units derived from non zwitterionic monomers, such as dimethyl- or diethylaminoethyl acrylate or methacrylate, or alkyl acrylates or methacrylates, acrylamides or methacrylamides, or vinyl acetate.

(5) Chitosan derived polymers comprising monomer units having following formulas:

(XIV)

(XV)

(XVI)

the unit (XIV) being present in amounts ranging from 0 to 30%, the unit (XV) being present in amounts ranging from 5 to 50% and the unit (XVI) being present in amounts ranging from 30 to 90%, wherein $R_{10}$ is chosen from a group of formula:

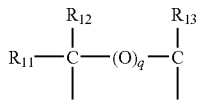
(XVII)

wherein, if q is 0, $R_{11}$, $R_{12}$ and $R_{13}$, which may be identical or different, are each chosen from hydrogen atoms, methyl radicals, hydroxyl radicals, acetoxy radicals and amino radicals, wherein the monoalkyl amine radicals and dialkyl amine radicals may be optionally interrupted with at least one nitrogen atom and/or optionally substituted with at least one amine, hydroxyl, carboxyl, alkylthio or sulfonic group, and alkylthio radicals, the alkyl group of which carries an amino radical, at least one of the $R_{17}$, $R_{18}$ or $R_{19}$ groups representing in this case a hydrogen atom;

or if q is 1, $R_{11}$, $R_{12}$ and $R_{13}$ each represent a hydrogen atom, as well as salts formed by these compounds with bases or acids.

(6) Polymers derived from the chitosan N-carboxyalkylation.

(7) Polymers having the following formula (XVIII) described for example in French Patent No. 1,400,366:

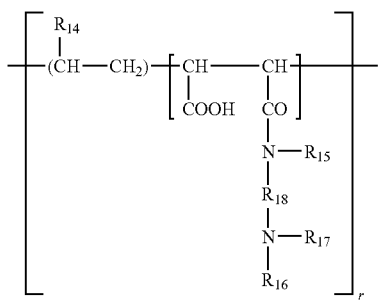
(XVIII)

wherein r is an integer greater than 1;

$R_{14}$ is chosen from hydrogen, $CH_3O$, $CH_3CH_2O$ and phenyls, $R_{15}$ is chosen from hydrogen and lower alkyl groups such as methyl or ethyl, $R_{16}$ is chosen from hydrogen and lower alkyl groups such as methyl or ethyl, $R_{17}$ is chosen from lower alkyl groups such as methyl, ethyl or a group having following formula: $-R_{18}-N(R_{16})_2$, wherein $R_{18}$ is chosen from $-CH_2CH_2-$, $-CH_2CH_2-CH_2-$, $-CH_2CH(CH_3)-$, $R_{16}$ being as defined above, as well as higher homologs of these groups comprising up to 6 carbon atoms.

(8) Amphoteric polymers of the -D-X-D-X type, chosen from:

a) polymers obtained from chloracetic acid or sodium chloracetate acting on compounds having at least one unit of formula:

-D-X-D-X-D-   (XIX)

wherein D is chosen from a group

and X is chosen from the symbol E or E', wherein E or E', which may be the same or different, are divalent groups chosen from linear chain or branched alkylene groups comprising up to 7 carbon atoms in the main chain, optionally substituted with hydroxyl groups, and which may comprise in addition oxygen, nitrogen and sulfur atoms, from 1 to 3 aromatic and/or heterocyclic rings; the oxygen, nitrogen and sulfur atoms being present in the form of ether, thioether, sulfoxide, sulfone, sulfonium, alkyl amine, alkenyl amine groups, hydroxyl, benzyl amine, amine oxide, quaternary ammonium, amide, imide, alcohol, ester and/or urethane groups.

b) Polymers of formula:

-D-X-D-X-   (XX)

wherein D is chosen from a group

and X is chosen from the symbol E or E', and at least one E', where E is as defined above and E' is a divalent group chosen from linear chain or branched alkylene groups comprising up to 7 carbon atoms in the main chain, optionally substituted with at least one hydroxyl group and comprising at least one nitrogen atom, the nitrogen atom being substituted with an alkyl chain optionally interrupted with an oxygen atom and comprising at least one carboxyl functionality or at least one hydroxyl functionality, betainized by reaction with chloracetic acid or sodium chloracetate.

(9) Copolymers of $(C_1-C_5)$alkyl vinyl ether/maleic anhydride partly modified by half-amidification with a N,N-dialkylaminoalkyl amine such as N,N-dimethylaminopropyl amine or by half-esterification with a N,N-dialkanol amine. These copolymers may also include other vinyl comonomers such as vinyl caprolactam.

According to at least one embodiment, fixing amphoteric polymers useful herein may be chosen from branched, block copolymers comprising:

(a) non ionic units derived from at least one monomer chosen from $C_1-C_{20}$ alkyl (meth)acrylates, N-mono($C_2-C_{12}$ alkyl)(meth)acrylamides and N,N-di($C_2-C_{12}$ alkyl) (meth)acrylamide, (b) anionic units derived from at least one monomer chosen from acrylic acid and methacrylic acid, and (c) polyfunctional units derived from at least one monomer comprising at least two polymerizable unsaturated functional groups, for example, having a structure made of hydrophobic blocks onto which several more hydrophilic blocks are bound through polyfunctional units (c).

Amphoteric polymers may, for example, have at least two glass transition temperatures (Tg), one of which at least is higher than 20° C. and the other lower than 20° C.

In at least one embodiment, amphoteric polymers may be chosen from polymers comprising units derived from:

(a) at least one monomer chosen from acrylamides and methacrylamides substituted on the nitrogen with an alkyl group, (b) at least one acidic comonomer comprising at least one reactive carboxylic moiety, and (c) at least one basic comonomer such as primary, secondary, tertiary and quaternary amine substituted esters of the methacrylic and acrylic acids, and the quaternization product of dimethylaminoethyl methacrylate with dimethyl or diethyl sulfate.

The amphoteric polymers may be chosen, for example, from polymers sold under the trade name AMPHOMER by NATIONAL STARCH.

In at least one embodiment, the at least one anionic or amphoteric fixing polymer is present in an amount ranging from 0.1 to 50%, for example, from 1 to 30%, relative to the total weight of said first composition.

Second Composition

A second composition may be applied onto the hair, prior to or after having applied the first composition comprising at least one solubilized fixing polymer.

In at least one embodiment, the second composition may comprise, in a cosmetically acceptable medium, at least one salt chosen from mineral salts and organic salts.

In at least one embodiment, the at least one anion of the at least one organic or mineral salt may be chosen from monovalent or polyvalent organic anions, and monovalent or polyvalent mineral anions.

In at least one embodiment, the at least one anion of the at least one organic or mineral salt may be chosen from nitrates, sulfates, carbonates, halides, for example, chlorides, bromates, phosphates and sulfonates.

In at least one embodiment, the at least one mineral or organic salt may be chosen from ammonium salts, alkaline metal salts, alkaline earth metal salts and transition metal salts.

For example, the metal may be chosen from copper, silver, gold, magnesium, sodium, potassium, calcium, iron, platinum, titanium, zinc and alloys thereof.

Further, for example, the at least one organic or mineral salt may be chosen from NaCl, $MgSO_4$, $ZnSO_4$, $ZnCl_2$, $MgCl_2$, $Na_2SO_4$, $Na_2CO_3$, $NH_4Cl$, $AgNO_3$, $Ag_2SO_4$, $Ag_2CO_3$, AgCl and their mixtures.

The salts may, for example, be chosen from NaCl and $MgSO_4$.

All these salts may optionally be hydrated.

The at least one mineral or organic salt may be present in an amount ranging from 0.15 to 30%, for example, from 0.5 to 20% by weight, relative to the total weight of the second composition.

As discussed above, the at least one anionic or amphoteric fixing polymer and the at least one mineral or organic salt are respectively present in the first and the second composition, each time in a cosmetically acceptable medium.

The cosmetically acceptable medium for the first and the second composition may be, for example, chosen from water, $C_1$-$C_6$ alcohols, for example, alkanols such as ethanol, propanol and isopropanol, alkane diols such as ethylene glycol, propylene glycol and pentane diol, benzyl alcohol, $C_5$-$C_{10}$ alkanes, acetone, methylethyl ketone, methyl acetate, butyl acetate, ethyl acetate, dimethoxyethane, diethoxyethane and mixtures thereof.

The first and/or the second composition may in addition comprise usual cosmetic additives chosen, for example, from thickeners, softeners, antifoaming agents, sunscreens, moisturizing agents, alkalinizing agents, dyes, pigments, fragrances, preserving agents, anionic, cationic, non ionic or amphoteric surfactants, non fixing polymers, volatile or non volatile silicones, vegetal, animal, mineral or synthetic oils, proteins, vitamins, polyols, and mixtures thereof.

The first composition and the second composition may be, for example, homogenous solutions, suspensions, water-in-oil emulsions, oil-in-water emulsions or multiple emulsions, all of them having a fluid consistency, that has been more or less thickened or gelled.

The pH value of the first and the second compositions may, for example, range from 4 to 10, for example 6 to 10 for the first composition and 4 to 8 for the second composition.

The pH value adjustment of these compositions may be effected by means of an alkaline agent, such as, for example, ammonia, monoethanol amine, diethanol amine, triethanol amine, 1,3-propane diamine, an alkaline hydroxide such as 2-amino-2-methyl-1-propanol or by means of an acidifying agent such as for example hydrochloric acid, acetic acid, lactic acid, oxalic acid or boric acid.

The hair shape may be given, for example, by the hand or with a comb, a brush or rollers whose diameters range from 2 to 30 mm.

As previously discussed, the fixing polymer is present in a solubilized form in the first composition.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the embodiments disclosed herein. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosed embodiments are approximations, unless otherwise indicated the numerical values set forth in the specific examples are reported as precisely as possible. Any numerical value, however, inherently contains certain errors necessarily resulting from the standard deviation found in their respective testing measurements.

The embodiments disclosed herein are illustrated in greater detail by the non-limiting example described below.

EXAMPLE

The method disclosed herein was implemented by using a first composition and a second composition.

The first and the second compositions had following formulations (AM stands for active materials):

First Composition:

| LUVISET Si PUR A (BASF) | 15 g AM |
|---|---|
| 2-amino-2-methyl-1-propanol | qs pH 9 |
| Ethanol | 10 g |
| Demineralized water | qs 100 g |

Second Composition:

| Ammonium chloride | 15 g |
|---|---|
| Demineralized water | qs 100 g, pH 5.5 |

The first composition was applied onto a portion of the hair. The hair was then shaped by the hand. The second composition was then applied and it was left on for five minutes at room temperature, then the hair was rinsed.

The treated portion according to the disclosure had a very satisfactory hair styling hold, that did resist shampoos. The hair was soft and felt very natural.

What is claimed is:

1. A semi permanent hair shaping method comprising:
   (a) applying onto the hair a first composition comprising, in a cosmetically acceptable medium, at least one solubilized fixing polymer chosen from anionic and amphoteric polymers, said application being optionally followed by a resting time for said first composition,
   (b) applying onto the hair a second composition comprising, in a cosmetically acceptable medium, at least 0.15% by weight, relative to the total weight of said second composition, of at least one salt chosen from mineral and organic salts, said application being optionally followed by a resting time for said second composition,
   where step b) is conducted prior to or after step a), then
   (c) rinsing the hair, and
   (d) shaping the hair either after applying the first composition of step a), or after applying the second composition of step b) and prior to the rinsing step c)
   wherein the semi permanent hair shaping method produces a hair shape that is remanent with respect to at least one shampoo.

2. A semi permanent hair shaping method according to claim 1, wherein said method does not comprise a step of opening the hair keratin disulfide bonds with a reducing composition or a step of re-forming said disulfide bonds with an oxidizing composition.

3. A semi permanent hair shaping method according to claim 1, wherein the at least one solubilized fixing polymer is an amphoteric polymer chosen from copolymers comprising units derived from:
   a) at least one monomer chosen from acrylamides and methacrylamides, optionally substituted on the nitrogen with an alkyl group,
   b) at least one acidic comonomer comprising at least one reactive carboxylic moiety, and
   c) at least one basic comonomer chosen from primary, secondary, tertiary and quaternary amine substituted esters of acrylic and methacrylic acids, and the quaternization product of dimethyl aminoethyl methacrylate with dimethyl or diethyl sulfate.

4. A semi permanent hair shaping method according to claim 1, wherein the at least one anionic polymer is chosen from copolymers of acrylic acid; copolymers derived from crotonic acid; polymers derived from maleic, fumaric, itaconic acids or anhydrides with vinyl ester, vinyl ethers, vinyl halides, phenyl vinyl derivatives, acrylic acid and esters thereof; anionic polyurethanes; elastomer or non elastomer, sulfoisophthalate group polymers; and anionic silicone graft polymers.

5. A semi permanent hair shaping method according to claim 1, wherein the at least one solubilized fixing polymer is present in an amount ranging from 0.1 to 50% by weight, relative to the total weight of said first composition.

6. A semi permanent hair shaping method according to claim 5, wherein the at least one solubilized fixing polymer is present in an amount ranging from 1 to 30% by weight, relative to the total weight of said first composition.

7. A semi permanent hair shaping method according to claim 1, wherein the at least one anion of the at least one organic or mineral salt is chosen from monovalent or polyvalent organic anions, monovalent or polyvalent mineral anions, and mineral sulfur anions.

8. A semi permanent hair shaping method according to claim 7, wherein the at least one anion is chosen from nitrates, sulfates, carbonates, and halides.

9. A semi permanent hair shaping method according to claim 7, wherein the at least one anion is chosen from chlorides, bromates, phosphates and sulfonates.

10. A semi permanent hair shaping method according to claim 1, wherein the at least one salt is chosen from ammonium salts, alkaline metal salts, alkaline earth metal salts and transition metal salts.

11. A semi permanent hair shaping method according to claim 10, wherein the metal is chosen from copper, silver, gold, iron, platinum, sodium, potassium, calcium, magnesium, titanium, zinc and alloys thereof.

12. A semi permanent hair shaping method according to claim 7, wherein at least one mineral or organic salt is chosen from $NaCl$, $MgSO_4$, $ZnSO_4$, $ZnCl_2$, $MgCl_2$, $Na_2SO_4$, $Na_2CO_3$, $NH_4Cl$, $AgNO_3$, $Ag_2SO_4$, $Ag_2CO_3$, $AgCl$ and mixtures thereof.

13. A semi permanent hair shaping method according to claim 1, wherein the at least one salt is present in an amount ranging from 0.15 to 30% by weight, relative to the total weight of said second composition.

14. A semi permanent hair shaping method according to claim 13, wherein the at least one salt is present in an amount ranging from 0.5 to 20% by weight, relative to the total weight of said second composition.

* * * * *

UNITED STATES PATENT AND TRADEMARK OFFICE
CERTIFICATE OF CORRECTION

PATENT NO. : 7,824,664 B2  Page 1 of 1
APPLICATION NO. : 11/414181
DATED : November 2, 2010
INVENTOR(S) : Priscille Devin-Baudoin It is certified that error appears in the above-identified patent and that said Letters Patent is hereby corrected as shown below:

Title page, item 57 (abstract), line 2, insert -- : -- after "comprising".

Title page, item 57 (abstract), line 3, "(c)" should read -- (a) --.

Title page, item 57 (abstract), line 8, "(d)" should read -- (b) --.

Signed and Sealed this

Twenty-second Day of February, 2011

David J. Kappos
*Director of the United States Patent and Trademark Office*